United States Patent [19]
Ueno et al.

[11] Patent Number: 5,945,301
[45] Date of Patent: Aug. 31, 1999

[54] KINASE IN TGF-β FAMILY SIGNAL TRANSDUCTION SYSTEM

[75] Inventors: Naoto Ueno, Sapporo; Kunihiro Matsumoto; Kenji Irie, both of Nagoya, all of Japan

[73] Assignee: Chugai Seiyaku Kabushiki Kaisha, Tokyo, Japan

[21] Appl. No.: 08/685,625

[22] Filed: Jul. 24, 1996

[30] Foreign Application Priority Data

Sep. 29, 1995 [JP] Japan ................................ 7-253549

[51] Int. Cl.⁶ .................................................. C12N 15/00
[52] U.S. Cl. .................. 435/69.1; 536/23.5; 530/350; 435/194; 435/183; 435/225.1; 435/225.2
[58] Field of Search .................. 536/23.5; 530/350; 435/69.1, 255.2, 255.21, 252.3, 183, 194

[56] References Cited

PUBLICATIONS

Shibuya et al, "Is AMK–1 a transfer molecule involved in TGF–β signal transduction," 68th Meeting of Japanese Biochemical Society, Sep. 15–18, 1995, Sendai, Japan (including English translation);.

Nishida et al, "Signaling pathways and functions of the MAP kinase superfamily," *Proceedings of the Japanese Cancer Association*, 54th Meeting of Japanese Cancer Association, Oct. 3–5, 1995, Kyoto, Japan (including English translation);.

Irie et al, "A novel member of MAPKKK, TAK1, may function as a mediator in TGF–β signal transduction," 18th Meeting of Japanese Molecular Biology Association, Dec. 6–9, 1995, Nagoya, Japan (including English translation);.

Yamaguchi et al, "Role of TAK1 kinase and its activator TAB1 in the TGF–β signaling pathway," 18th Meeting of Japanese Molecular Biology Society, Dec. 6–9, 1995, Nagoya, Japan (including English translations);.

Yamaguchi et al "Identification of a Member of the MAP–KKK Family as a Potential Mediator of TGF–β Signal Transduction," Science, vol. 270 (Dec. 22, 1995) pp. 2008–2011.

George et al., Macromolecular Sequencing and synthesis, Selected Methods and applications, pp. 127–149, Alan R. Liss, Inc., 1988.

*Primary Examiner*—Lila Feisee
*Assistant Examiner*—Eliane Lazar-Wesley
*Attorney, Agent, or Firm*—Burns, Doane, Swecker & Mathis, L.L.P.

[57] ABSTRACT

The invention relates to a kinase which is activated by transforming growth factor-β (TGF-β) and funstions in the TGF-β family signal tranduction system. The invention further relates to a process of producing said kinase and to a gene encoding said kinase.

40 Claims, 11 Drawing Sheets

Fig.5A

```
  1'  ATGTCTACAGCCTCTGCCGCCTCCTCCTCGTCTTCGGCCGGTGAGATGATCGAA
      ****** ******* ****** ****** ***  ** ***************
  1"  ATGTCGACAGCCTCCGCCGCCTCCTCCTCGTCTTCTGCCAGTGAGATGATCGAA

61'  GCCCCTTCCCAGGTCCTCAACTTTGAAGAGATCGACTACAAGGAGATCGAGGTGGAAGAG
      ** * ****************** *********************************
 61"  GCGCCGTCGCAGGTCCTGAACTTCGAAGAGATCGACTACAAGGAGATCGAGGTGGAAGAG

121'  GTTGTTGGAAGAGGAGCCTTTGGAGTTGTTTGCAAAGCTAAGTGGAGAGCAAAAGATGTT
      *** ***************** ************************************
121"  GTTGTCGGAAGAGGAGCTTTTGGAGTAGTTTGCAAAGCTAAGTGGAGAGCAAAAGATGTC

181'  GCTATTAAACAAATAGAAAGTGAATCTGAGAGGAAAGCGTTTATTGTAGAGCTTCGGCAG
      ************ ***** **********  ***  *** *  ** ***********
181"  GCTATTAAACAGATAGAAAGTGAGTCTGAGAGGAAGGCTTTCATTGTGGAGCTCCGGCAG

241'  TTATCCCGTGTGAACCATCCTAATATATTGTAAAGCTTTATGGAGCCTGCTTGAATCCAGTG
      ** ** ******* ***********  *** ***  *  ** *** *************
241"  TTGTCGCGTGTGAACCATCCTAACATTGTCAAGTTGTACGGAGCCTGCCTGAATCCAGTA

301'  TGTCTTGTGATGGAATATGCTGAAGGGGCTCTTTATATAAATGTGCTGCATGGTGCTGAA
      ****************************** ***** ** ********************
301"  TGTCTTGTGATGGAATATGCAGAGGGGGCTCTTGTATAATGTGCTGTATAATGTGCTGCATGGTGCTGAA
```

Fig.5B

```
361'  CCATTGCCATATATTATACTGCTGCCCACGCAATGAGTTGGTGTTTACAGTGTTCCCAAGGA
      ********** ** ** ********* ** ** ****** ************ ********
361"  CCATTGCCTTACTACACTGCTGCTCATGCCATGAGCTGGTGTTTACAGTGTTCCCAAGGA

421'  GTGGCTTATCTTCACAGCATGCAAACCCAAAAGCGCTAATTCACAGGGACCTGAAACCACCA
      ****** ** ******** ***** ****** ********** ** * ** ***** *
421"  GTGGCTTACCTGCACAGCATGCAGCCCAAAAGCGCTGATTCACAGGGACCTCAAGCCCTCCA

481'  AACTTACTGCTGGTTGCAGGGGGACAGTTCTAAAAATTTGTGATTTTGGTACAGCCTGT
      ********* ****************************** ** ***** ***********
481"  AACTTGCTGCTGGTTGCAGGAGGACAGTTCTAAAAATCTGCGATTTTGGTACAGCTTGT

541'  GACATTCAGACACACATGACCAATAACAAGGGGAGTGCTGCTTGGATGGCACCTGAAGTT
      *** ** *** ****** ********** ***** ** ************* *******
541"  GACATCCAAACACACATGACCAATAATAAAGGGAGTGCTGCTTGGATGGCCTGAAGTG

601'  TTTGAAGGTAGTAATTACAGTGAAAAATGTGACGTCTTCAGCTGGGGTATTATTCTTTGG
      *********** ****** ******* ***** ** ********* ****** ** ***
601"  TTTGAAGGTAGCAATTACAGTGAAAAAGTGTGATGTCTTCAGCTGGGGTATTATCCCTCTGG
```

Fig.5C

```
661'  GAAGTGATAACGCGTCGGAAACCCTTTGATGAGATTGGTGGCCCAGCTTTCCGAATCATG
      ****  ******   *********************   ************************
661"  GAAGTGATAACACGCCCGGAAACCCTTCGATGAGATCGGTGGCCCAGCTTTCAGAATCATG

721'  TGGGCTGTTCATAATGGTACTCGACCACCACTGATAAAAAAATTTACCTAAGCCCATTGAG
      ***  ******   ***** *********************   ****************
721"  TGGGCTGTTCATAATGGCACTCGACCACCACTGATCAAAAATTTACCTAAGCCCATTGAG

781'  AGCCTGATGACTCGTTGTTGGTCTAAAGATCCTTCCCAGCGCCCTTCAATGGAGGAAATT
      *** ****** ****  *********************   *******************
781"  AGCTTGATGACACGCTGTTGGTCTAAGGACCCATCTCAGCGCCCCATCAATGGAGGAAATT

841'  GTGAAAAATAATGACTCACTTGATGCGGTACTTTCCAGGAGCAGATGAGCCATTACAGTAT
      *** *****************  *********************   *************
841"  GTGAAAAATAATGACTCACTTGATGCGGTACTTCCCAGGAGCGGATGAGCCATTACAGTAT

901'  CCTTGTCAGTATTCAGATGAAGGACAGAGAGCAACTCTGCCACCAGTACAGGCTCATTCATG
      ****** *******   *********************   *******************
901"  CCTTGTCAGTACTCTGATGAAGGGCAGAGAGCAACTCAGCCACCACCAGCACCAGGCTCGTTCATG

961'  GACATTGCTTCTACAAATACGAGTAACAAAAGTGACACTAATATGGAGCAAGTTCCTGCC
      *********************   *  *    *********************************
961"  GACATTGCTTCTACAAATACCAGTAATAAAAGTGACACAAATATGGAACAGGTTCCTGCC
```

Fig. 5D

```
1021'  ACAAATGATACTATTAAGCGCTTAGAATCAAAATTGTTGAAAAATCAGGCAAAGCAACAG
       ***** ** ******** ****** ** ****** ****** ************
1021"  ACAAACGACACTATTAAACGCTTGGAGTCAAAACTGTTGAAAAACCAGGCAAAGCAACAG

1081'  AGTGAATCTGGACGTTTAAGCTTGGGAGCCTCCCATGGGAGCAGTGTGGAGAGCTTGCCC
       ***** ************ * * * *************************
1081"  AGTGAATCTGGACGCCTGAGCTTGGGAGCCTCTCGTGGGAGCAGTGTGGAGAGCTTGCCC

1141'  CCAACCTCTGAGGGCAAGAGGATGAGTGCTGACATGTCTGAAATAGAAGCTAGGATCGCC
       ** * ** ****************************************** ******
1141"  CCCACTTCCGAGGGCAAGAGGATGAGTGCTGACATGTCTGAAATAGAAGCCAGGATCGTG

1201'  GCAACCACAGGCAACGGACAGCCAAGACGTAGATCCATCCAAGACTTGACTGTAACTGGA
       ** ** **** ****** ** * ****** ************************
1201"  GCGACTGCAGTGAACGGGCAACCAAGGCGTAGATCCATCCAAGACTTGACTGTTACTGGG

1261'  ACAGAACCTGGTCAGGTGAGCAGTAGGTCATCCAGTCCCAGTGTCAGAATGATTACTACC
       ************ ***** ******** ** ***** *************** ******
1261"  ACAGAACCTGGTCAGGTGAGCAGTGAGCAGCCGGTCATCCAGCCCTAGTGTCAGAATGATCACTACC

1321'  TCAGGACCAACCTCAGAAAAGCCAACTCGAAGTCATCCATGGACCCCTGATGATTCCACA
       ************* ***** ****** ***** ************************
1321"  TCAGGACCAACCTCAGAGAAGCCAGCTCGCCAGTCACCCATGGACCCCTGATGATTCCACA
```

Fig.5E

```
1381'  GATACCAATGGATCAGATAACTCCATCCCAATGGCTTATCTTACACTGGATCACCAACTA
       ***********   *************************  ******************
1381"  GACACCAATGGCTCAGATAACTCCATCCCAATGGCGTATCTTACACTGGATCACCAGCTA

1441'  CAGCCTCTAGCACCGTGCCCAAACTCCAAAGAATCTATGGCAGTGTTTGAACAGCATTGT
       **********  ************************  **********************
1441"  CAGCCTCTAGCGCCGTGCCCAAACTCCAAAGAATCCATGGCAGTGTTCGAACAGCACTGT

1501'  AAAATGGCACAAGAATATATGAAAGTTCAAACAGAAATTGCATTGTTATTACAGAGAAAG
       ************  ** **********************  *******************
1501"  AAAATGGCACAGGAGTATATGAAAGTTCAAACCGAAATCGCATTGTTACTACAGAGAAAG

1561'  CAAGAACTAGTTGCAGAACTGGACCAGGATGAAAAGGACCAGCAAAATACATCTCGCCTG
       ***************  ***********************************  **  *
1561"  CAAGAACTAGTTGCAGAATTGGACCAGGATGAAAAGGACCAGCAAAATACATCTCGTCTG

1621'  GTACAGGAACATAAAAAGCTTTTAGATGAAAACAAAAGCCTTTCTACTTACTACCAGCAA
       *********************************************  ********
1621"  GTACAGGAACATAAAAAGCTTTTAGATGAAAACAAAAGCCTTTCTACTTATTACCAGCAA

1681'  TGCAAAAAACAACTAGAGGTCATCAGAAGTCAGCAGAAACGACAAGGCACTTCATGA
       *********************************  **********************
1681"  TGCAAAAAACAACTAGAGGTCATCAGAAGTCAGCAGAAACGACAAGGCACTTCATGA
```

Fig.6A

```
  1'  MSTASAASSSSSSAGEMIEAPSQVLNFEEIDYKEIEVEEVVGRGAFGVVCKAKWRAKDV
      ************  * ******************************************
  1"  MSTASAASSSSSSASEMIEAPSQVLNFEEIDYKEIEVEEVVGRGAFGVVCKAKWRAKDV

61'  AIKQIESESERKAFIVELRQLSRVNHPNIVKLYGACLNPVCLVMEYAEGGSLYNVLHGAE
      ***********************************************************
 61"  AIKQIESESERKAFIVELRQLSRVNHPNIVKLYGACLNPVCLVMEYAEGGSLYNVLHGAE

121'  PLPYYTAAHAMSWCLQCSQGVAYLHSMQPKALIHRDLKPPNLLLVAGGTVLKICDFGTAC
      ***********************************************************
121"  PLPYYTAAHAMSWCLQCSQGVAYLHSMQPKALIHRDLKPPNLLLVAGGTVLKICDFGTAC

181'  DIQTHMTNNKGSAAWMAPEVFEGSNYSEKCDVFSWGIILWEVITRRKPFDEIGGPAFRIM
      ***********************************************************
181"  DIQTHMTNNKGSAAWMAPEVFEGSNYSEKCDVFSWGIILWEVITRRKPFDEIGGPAFRIM

241'  WAVHNGTRPPLIKNLPKPIESLMTRCWSKDPSQRPSMEEIVKIMTHLMRYFPGADEPLQY
      ***********************************************************
241"  WAVHNGTRPPLIKNLPKPIESLMTRCWSKDPSQRPSMEEIVKIMTHLMRYFPGADEPLQY
```

Fig.6B

```
301'  PCQYSDEGQSNSATSTGSFMDIASTNTSNKSDTNMEQVPATNDTIKRLESKLLKNQAKQQ
      ************************************************************
301"  PCQYSDEGQSNSATSTGSFMDIASTNTSNKSDTNMEQVPATNDTIKRLESKLLKNQAKQQ

361'  SESGRLSLGASHGSSVESLPPTSEGKRMSADMSEIEARIAATTGNGQPRRSIQDLTVTG
      *********.************************************.*..********
361"  SESGRLSLGASRGSSVESLPPTSEGKRMSADMSEIEARIVATAGNGQPRRSIQDLTVTG

421'  TEPGQVSSRSSSPSVRMITTSGPTSEKPTRSHPWTPDDSTDTNGSDNSIPMAYLTLDHQL
      **********************.***********.*************************
421"  TEPGQVSSRSSSPSVRMITTSGPTSEKPARSHPWTPDDSTDTNGSDNSIPMAYLTLDHQL

481'  QPLAPCPNSKESMAVFEQHCKMAQEYMKVQTEIALLLQRKQELVAELDQDEKDQQNTSRL
      ************************************************************
481"  QPLAPCPNSKESMAVFEQHCKMAQEYMKVQTEIALLLQRKQELVAELDQDEKDQQNTSRL

541'  VQEHKKLLDENKSLSTYYQQCKKQLEVIRSQQQKRQGTS
      **************************************
541"  VQEHKKLLDENKSLSTYYQQCKKQLEVIRSQQQKRQGTS
```

KINASE IN TGF-β FAMILY SIGNAL TRANSDUCTION SYSTEM

BACKGROUND OF THE INVENTION

1. Field of Invention

The present invention relates to a kinase which is activated by transforming growth factory-β (TGF-β) and functions in the TGF-β family signal transduction system (transforming growth factor-activated kinase: TAK1), to a process for production thereof, and to a gene coding for it. TAK1, also known as an activator of MAPK kinase (AMK-1), is an enzyme (a kinase) which is activated by TGF-β and BMP (bone morphogenetic protein) and in turn activates MAPK kinase by phosphorylation.

2. Related Art

The receptors of TGF-β superfamily comprise Ser/Thr kinases in the cytoplasmic region, and are classified into type I which has a repeating sequence of Gly-Ser (GS box) at the amino terminal proximal to the transmembrane domain, and type II which does not have the GS box. It is believed that, in the case of TGF-β, ligands form complexes with type I receptors after binding to type II receptors, and the kinases constitutively active type II receptors phosphorylate the type I receptors in the vicinity of the GS box, thus activating the type I receptors for transduce the signal from those ligands into the cell. However, virtually nothing is known about the signal-transducing molecules downstream from these receptors.

According to the known signal transducing cascade from extracellular mating pheromones to mating in the eukaryotic budding yeast Saccharomyces cerevisiae, G protein is activated by the mating pheromone, G protein activates MAPKK kinase (MAPKKK) (Ste11), the activated MAPKKK activates MAPK kinase (MAPKK) by phosphorylation, the thus activated MAPKK (Ste7) in turn activates MAP kinase (mitogen-activated protein kinase: MAPK) by phosphorylation, and finally MAPK activates FUSI protein, which initiates mating of the cells.

SUMMARY OF INVENTION

It is an object of the present invention to provide a novel factor which is located downstream of the mammalian receptor of the TGF-β receptor signal transducing system and contributes to transduce those signals, a gene coding for it, and a method of producing the gene.

In attempting to achieve this object, the present inventors have succeeded in introducing mouse-derived DNA into Saccharomyces cerevisiae yeast lacking activity of MAP-KKK (Ste11) in the above-mentioned mating pheromone signaling cascade, screening for cDNA capable of complementing the activity-lacking MAPKKK, and cloning the cDNA capable of complementing the activity-lacking MAPKKK, thus completing the present invention.

Thus, the present invention provides DNA coding for a polypeptide with kinase activity which is activated by TGF-β and comprises the amino acid sequence of SEQ ID NO: 1 from Ser at position 23 to Ser at position 579, or an amino acid sequence which has a modification of the amino acid sequence wherein one to a few amino acids are added, deleted and/or substituted with other amino acids. According to one embodiment thereof, the DNA has the nucleotide sequence of SEQ ID NO: 1 from T at position 223 to A at position 1893.

The present invention further provides DNA coding for a polypeptide with kinase activity which is activated by TGF-β and comprises the amino acid sequence of SEQ ID NO: 1 from Met at position 1 to Ser at position 579, or an amino acid sequence which has a modification of said amino acid sequence wherein one to a few amino acids are added, deleted and/or substituted with other amino acids. According to one embodiment thereof, the DNA has the nucleotide sequence of SEQ ID NO: 1 from A at position 157 to A at position 1893.

The present invention further provides DNA coding for a polypeptide with kinase activity which is activated by TGF-β and has at least 80% homology with the nucleotide sequence of SEQ ID NO: 1. The invention still further provides DNA coding for a polypeptide with kinase activity which is activated by TGF-β and is capable of hybridizing with the nucleotide sequence of SEQ ID NO: 1 under conditions of 60° C., 0.1×SSC and 0.1% SDS.

The present invention provides DNA coding for a polypeptide with kinase activity which is activated by TGF-β and comprises the amino acid sequence of SEQ ID NO: 5 from Ser at position 23 to Ser at position 579, or an amino acid sequence which has a modification of said amino acid sequence wherein one to a few amino acids are added, deleted and/or substituted with other amino acids. According to one embodiment thereof, the DNA has the nucleotide seuquence of SEQ ID NO: 5 from T at position 249 to A at position 1919.

The present invention further provides DNA coding for a polypeptide with kinase activity which is activated by TGF-β and comprises the amino acid sequence of SEQ ID NO: 5 from Met at position 1 to Ser at position 579, or an amino acid sequence which has a modification of said amino acid sequence wherein one to a few amino acids are added, deleted and/or substituted with other amino acids. According to one embodiment thereof, the DNA has the nucleotide sequence of SEQ ID NO: 5 from A at position 183 to A at position 1919.

The present invention further provides DNA coding for a polypeptide with kinase activity which is activated by TGF-β and has at least 80% homology with the nucleotide sequence of SEQ ID NO: 5. The present invention still further provides DNA coding for a polypeptide with kinase activity which is activated by TGF-β and is capable of hybridizing with the nucleotide sequence of SEQ ID NO: 5 under conditions of 60° C., 0.1×SSC and 0.1% SDS.

The present invention still further provides a method of producing a polypeptide with kinase activity which is activated by TGF-β, characterized by culturing host cells transformed with a vector comprising any of the above-mentioned DNA, and recovering the expressed product from the culture. The invention still further provides a polypeptide with kinase activity which is activated by TGF-β and is produced by this method. The polypeptide is expected to have the amino acid sequence of SEQ ID NO: 1 from Ser at position 23 to Ser at position 579 or the amino acid sequence of SEQ ID NO: 5 from Ser at position 23 to Ser at position 579. Thus, the invention still further provides a kinase enzyme which is activated by TGF-β and has these amino acid sequence.

BRIEF DESCRIPTION OF THE DRAWINGS

FIGS. 5A to 5E compare nucleotide sequence of mouse TAK1 and that of human TAK1.

FIGS. 6A to 6B compare amino acid sequence of mouse TAK1 and that of human TAK1.

DETAILED DESCRIPTION

Figure 1:
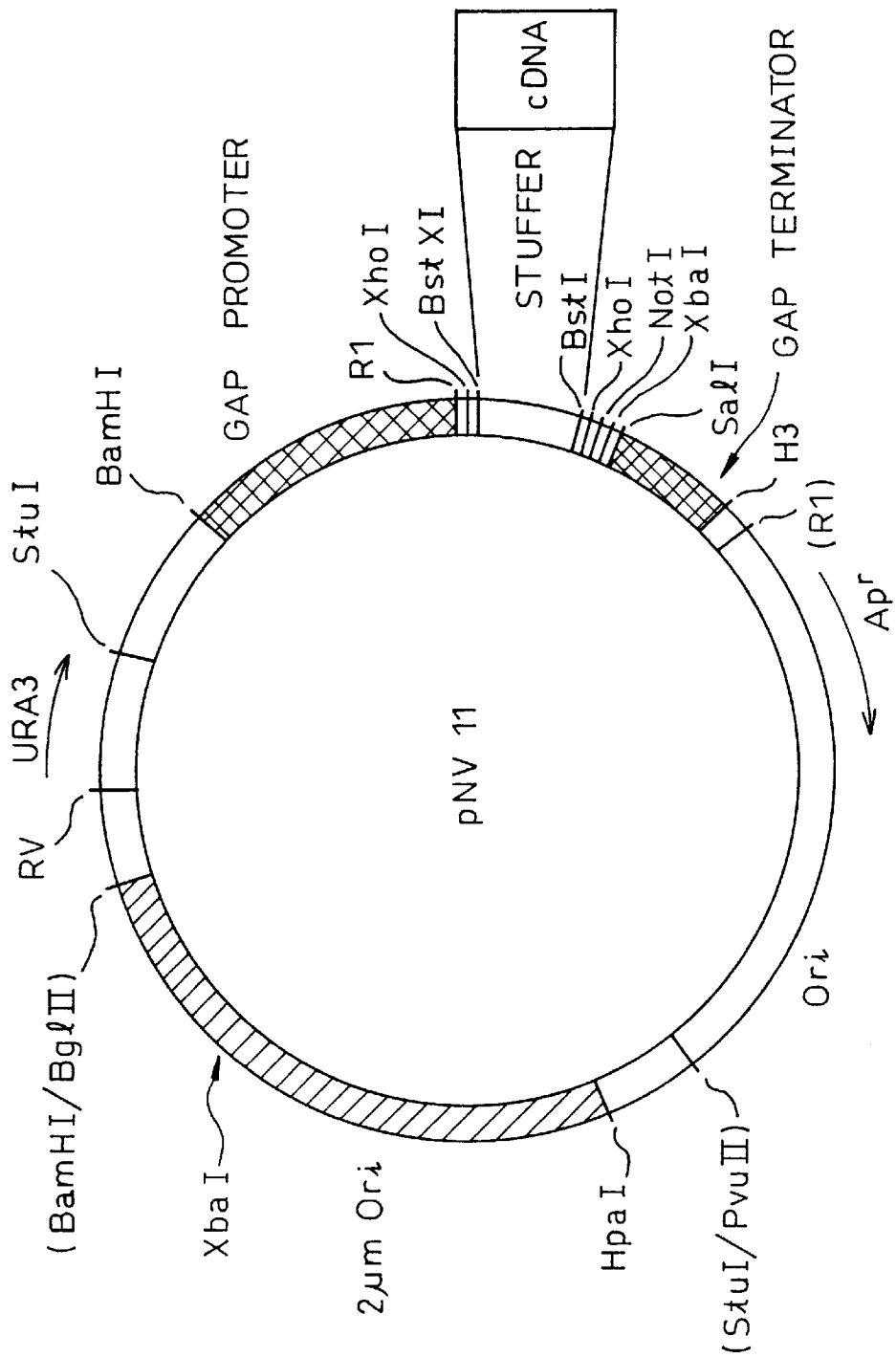
FIG. 1 shows the yeast expression vector pNV11.

According to the present invention, a gene may be cloned, for example, by introducing an expression vector containing mammalian cDNA into yeast which lacks MAPKKK activity and has a reporter gene which is easily detectable at the end of the cascade, and detecting whether cDNA which complements the lacking MAPKKK activity has been inserted based on expression of the reporter gene. Also other yeast, for example, lacking Ssk2/Ssk22 and Sho1 activities which works under a high osmotic pressure stress signal transducing system can be used.

The detection system used may be the MAPK cascade which transduces the intracellular signaling for the mating pheromone in *Saccharomyces cerevisiae* (I. Herskowitz, Cell, Vol.80, 187 (1995); D. E. Lein et., Curr. Opin. Cell Biol. Vol. 7, 197 (1995); J. Schulz et al., Curr. Opin. Gene Dev., Vol. 5, 31 (1995)). The normal signaling cascade in this system includes Ste 11 kinase, Ste 7 kinase and Fus 3/Kss 1 kinase, which correspond to MAPKKK, MAPKK and MAPK, respectively. Ste 11, Ste 7 and Fus 3/Kss 1 act in succession to transduce signals to the transcription factor Ste 12, and Ste 12 in turn activates transcription of mating specific genes such as FUS 1.

For screening the cDNA, there may be used a cascade including a functional mutation of Ste 7 (STE7$^{P368}$) and a deletion mutation of Ste 11 (Ste11Δ) from the above-mentioned cascades (K. Irie et al., Science Vol. 265, 1716 (1994)), and it has been confirmed that when this system is monitored based on the histidine-expressing phenotype imparted by the reporter gene FUS1p::HIS3 corresponding to the mating pathway, the activated form of either mammalian Raf or MEKK (RafΔN and MEKKΔN, respectively) can replace Ste 11 activity deficiency in an Ste7$^{P368}$ dependent manner. Thus, by introducing test cDNA into yeast with the above-mentioned mutated cascade and detecting the histidine-expressing phenotype, it is possible to select cDNA capable of complementing Ste11Δ (MAPKKK deficiency).

The test cDNA library used may be any mammalian-derived cDNA library, an example of which is a cDNA expression library from a mouse cell line, such as the mouse cell line BAF-BO3. This cDNA library is obtained by cloning cDNA corresponding to poly(A)-RNA from the mouse IL-3-dependent pro-β cell line BAF-BO3, under the control of the TDH3 promoter of the yeast expression vector pNV11. Another example of the test cDNA library used may be a cDNA expression library from a human cell line, such as the human cell line Jurkat.

The above-mentioned cDNA library was screened with the screening system described above to obtain a positive clone. The nucleotide sequence of the cDNA of this clone and the amino acid sequence encoded thereby correspond to nucleotides 223–1893 and amino acids 23–579 of SEQ ID NO: 1. The cDNA library from a human cell line may be screened according to the above-mentioned screening system. Alternatively, the cDNA library from a human cell line may be screened using as a probe a mouse cDNA obtained as described above. The nucleotide sequence of the cDNA of another positive clone and the amino acid sequence encoded thereby correspond to nucleotides 249–1919 and amino acids 23–579 of SEQ ID NO: 5.

To obtain longer cDNA (full-length cDNA), the above-mentioned cDNA was used as a probe for screening of the cDNA library to obtain positive clones. These clones had a 5'-elongated portion of about 230 bp with respect to the cDNA. The cDNA with the 5'-elongated end was named TAKL cDNA, and the originally cloned cDNA without the 5'-elongated end was named TAK1ΔN cDNA. The nucleotide sequence of TAK1 cDNA is represented by nucleotides 1 to 2443 of SEQ ID NO: 1, and the amino acid sequence encoded thereby is represented by amino acids 1 to 579 of SEQ ID NO: 1. The protein and polypeptide represented by this amino acid sequence are referred to as the TAK1 protein and polypeptide. The protein and polypeptide represented by the amino acid sequence encoded by TAK1ΔN cDNA are referred to as TAK1ΔN protein and polypeptide. In addition, the nucleotide sequence of human TAK1 cDNA is represented by nucleotides 1 to 2656 of SEQ ID NO: 5, and the amino acid sequence encoded thereby is represented by amino acids 1 to 579 of SEQ ID NO: 5.

The primary amino acid sequence of TAK1 protein suggests that the protein has an N-terminal protein kinase catalitic domain and a C-terminal domain of approximately 300 amino acid residues. The catalitic domain includes a consensus sequence corresponding to the protein kinase subdomains I–XI (S. K. Hanks et al., Science 241, 42 (1988)). This catalyst domain has approximately 30% homology with the amino acid sequence of the catalyst domains of Raf-1 (T. I. Bonner et al., Nucleic Acids Res., Vol.14, 1009 (1986)) and MEKK (C. A. Langer-Carter et al., Science Vol. 260, 315 (1993)). The sequence of 300 C-terminal amino acid residues continuing from the catalyst domain has no significant homology with other proteins.

The TAK1ΔN cDNA lacking the codons for 22 N-terminal amino acids may be introduced into yeast with the Ste11Δ mutation to complement the Ste11Δ mutation (MAPKKK deficiency), but when the full-length TAK1 cDNA is introduced into the Ste11Δ mutant it does not complement the Ste11Δ mutation. Consequently it is believed that TAK1 kinase is activated by removal of the 22 N-terminal amino acids.

Thus, the present invention provides DNA coding for a polypeptide comprising the amino acid sequence of SEQ ID NO: 1 from Met at position 1 to Ser at position 579. This DNA includes, as typical examples, DNA coding for the polypeptide comprising the amino acid sequence from the 23rd amino acid Ser to the 579th amino acid Ser, and DNA coding for the polypeptide comprising the amino acid sequence from the 30th amino acid Glu to the 295th amino acid Asp. However, the DNA of the present invention is not limited to these, and also encompasses DNAs coding for polypeptides consisting of amino acid sequences from any of the amino acids between the 1st Met to the 30th Glu, to the 295th amino acid Asp. It will be readily recognized that even DNA coding for a polypeptide with an elongated N-terminus may be used to obtain an active enzyme by processing of the polypeptide after expression, and that lack of a C-terminal region other than the kinase will still give the same kinase activity.

Also, the present invention provides DNA coding for a polypeptide comprising an amino acid sequence of SEQ ID NO: 5 from Ser at position 23 to Ser at position 579. This DNA includes, as typical examples, DNA coding for a polypeptide having an amino acid sequence from the first Ser to the 579th amino acid Ser and DNA coding for a polypeptide having an amino acid sequence from 23rd amino acid Ser to the 579th amino acid Ser.

The present invention also encompasses DNAs coding for polypeptides which have modifications of the polypeptides with the various amino acid sequences mentioned above, and maintain kinase activity by activation by TGF-β (referred to as TAK1 activity). Such a modification is intended to mean that the aforementioned amino acid sequences of various lengths from the amino acid sequence represented by SEQ ID NO: 1 or SEQ ID NO: 5 may have one to a few, such as about 1 to 10 or 1 to 5, amino acids added, deleted and/or substituted with other amino acids. In a more general sense, the present invention encompasses DNA coding for a polypeptide with an amino acid sequence which has at least 80%, preferably at least 90% and more preferably at least 95% homology with the amino acid sequence of SEQ ID NO: 1 or SEQ ID NO: 5 and maintains TAK1 activity.

The present invention also encompasses DNA coding for a polypeptide which is capable of hybridizing with the nucleotide sequence represented by SEQ ID NO: 1 or SEQ ID NO: 5 under conditions of, for example, 60° C., 0.1×SSC and 0.1% SDS, and maintains TAK1 activity. Here, the 0.1×SSC may be a 200-fold dilution of 20×SSC comprising 3 M NaCl and 0.3 M sodium citrate.

The present invention further provides polypeptides or proteins with amino acid sequences corresponding to the various DNA nucleotide sequences mentioned above, and particularly to polypeptides and proteins which maintain TAK1 activity. As a more concrete example, the present invention relates to a polypeptide or protein expressed by introduction of any of the aforementioned DNA into host cells, which may be animal cells or microorganic cells, as an insertion into, for example, a vector, particularly an expression vector, and particularly to polypeptides and proteins with TAK1 activity.

A polypeptide or protein according to the invention typically has an amino acid sequence selected from the amino acid sequence represented by SEQ ID NO: 1 or SEQ ID NO: 5, starting from any of the amino acids between the 1st amino acid Met and the 23rd amino acid Ser (inclusive) and continuing to the 579th amino acid Ser.

The present invention also encompasses polypeptides and proteins with amino acid sequences based on the above-mentioned amino acid sequence and modified by one to a few, such as about 1 to 10 or 1 to 5 amino acids added, deleted and/or substituted with other amino acids. They preferably have TAK1 activity. The invention further relates to polypeptides and proteins with amino acid sequences having at least 80%, preferably at least 90% and more preferably at least 95% homology with all or a portion of the amino acid sequence of SEQ ID NO: 1 or SEQ ID NO: 5, and which maintain TAK1 activity.

As described above, cDNA coding for human TAK1 can be obtained by using that of the mouse TAK1 and Examples 5 and 6 demonstrate the isolation of cDNA coding for human TAK1.

The various DNA according to the invention may be cloned from animal cells as cDNA by the method described in Example 2, for example. DNA which has been mutated or modified with respect to the native cDNA may be prepared by common means such as, for example, using the native cDNA as a template for PCR amplification, site-specific mutagenic treatment, etc.

A polypeptide or protein according to the invention may be obtained by expressing the corresponding DNA in a suitable host. The host in this case may be a eukaryote such as cultured cells of higher eukaryotic organisms including humans, monkeys, mice, hamsters, frogs, etc., examples of which include THP-1 cells, MC3T3-E1 cells, XTC cells, MvlLu cells, CHO cells and COS cells; lower eukaryotic cells including filamentous fungi such as Aspergillus, such as *Aspergillus niger*; and yeast such as Saccharomyces, such as *Saccharomyces cerevisiae*. The host cells may also be prokaryotic cells, for example bacteria such as *Escherichia coli*.

When the desired DNA is expressed in such hosts, a promoter and other expression regulating sequences suitable for the host are used. For example, for expression in animal cells, plasmids with various promoters, e.g. pCDM8, pSV, pEF, etc. are used, whereas in yeast hosts a plasmid such as pNV11 is used and in *E. coli* a plasmid such as pGEMEX or pUEX is used.

The culturing of the transformed host may be carried out by a conventional method. The recovery and purification of the polypeptide or protein from the cultured product may be accomplished by any method commonly employed for the purification of enzymes, such as centrifugation, filtration, gel filtration chromatography, affinity chromatography, or the like.

Kinases activated by TGF-β, i.e. kinases in the TGF-β family signal transduction system, are useful for the detection of agents which inhibit or promote signal transduce by TGF-β and its super family, which are known to be involved in a large number of disorders.

EXAMPLES

The present invention will now be explained in more detail by way of the following examples.

Example 1

Preparation of cDNA library

A conventional method was used to synthesize cDNA from poly(A)-RNA of a mouse IL-3-dependent cell line BAF-BO3, which was then introduced into a yeast expression vector pNV11 shown in FIG. 1 (Ninomiya-Tsuji, J. et al., Proc. Natl. Acad. Sci. USA 88, 9006–9010 (1991)) under the control of TDH3 promoter, to prepare a cDNA library.

Example 2

Screening of cDNA library

The cDNA library prepared in Example 1 was screened using *Saccharomyces cerevisiae* SY1984-P (his3Δ, Ste11Δ, FUS1p:HIS3, STE7P368). In the signal transducing system of the mating pheromone for this yeast, Ste 11 is mutated causing loss of function, the serine at position 368 of Ste-7 is replaced with proline, and the FUS1 upstream activating sequence is linked to the HIS3 open reading frame to form a reporter gene. This yeast line lacks the native his3, and therefore can only grow when exogenous histidine is present in the culture or when the Ste11 activity lost by the mutation is complemented.

*S. cerevisiae* SY1984-P was transformed with one of various different plasmids. The plasmids used were YCplac22 (vector), pRS314PGKMEKKCT (expressing MEKKΔN which lacks the N-terminal domain downstream of the PGK1 promoter (K. J. Blumer et al., Proc. Natl. Acad. Sci. USA, Vol.91, 4925 (1994)) and pADU-RafΔN (expressing RafΔN which lacks the N-terminal domain from the ADH1 promoter (K. Irie et al., Science, Vol.265, 1716 (1994))). These transformants were applied to SC-His plates without histidine, and incubated at 30° C. As a result, the yeast transformed with YCplac22 vector failed to growth, whereas the yeasts transformed with pRS314PGKMEKKCT and pADU-RafΔN did reproduce. The validity of the screening system was thus confirmed.

The screening system yeast line YS1984-P was transformed with the cDNA library prepared in Example 1 and screened on an SC-His plate, yielding the positive clone pNV11-HU11. The cDNA of this clone was named TAK1ΔN cDNA. The nucleotide sequence of this cDNA was determined by the dideoxynucleotide chain termination method. The nucleotide sequence corresponds to the sequence of nucleotides 223 to 1893 of Sequence No.1, and the amino acid sequence encoded thereby corresponds to amino acids 23 (Ser) to 579 (Ser) of the amino acid sequence of SEQ ID NO: 1.

The aforementioned TAK1ΔN cDNA was radioactively labelled and used as a probe for cloning of the full-length cDNA, and the cDNA library obtained in Example 1 was further screened. Positive clones were thus obtained. The cDNA of these clones were subcloned at the EcoRI site of vector pBS (product of Stratagene) to obtain pBS-TAK1-5'. This clone was the full-length clone containing the initiation codon ATG. The cDNA was named TAK1 cDNA. Its nucleotide sequence is represented by SEQ ID NO: 1. The full-length amino acid sequence from Met at position 1 to Ser at position 579 is encoded by nucleotides 1 to 2443 of this sequence.

Example 3

Distribution of TAK1 gene in tissues

Total RNA was extracted from different mouse tissues, and radioactively labelled TAK1 cDNA was used as a probe for Northern blotting, which revealed expression of TAK1 cDNA-hybridizing RNA in all of the tissues and organs tested (spleen, thymus, lungs, heart, liver and brain). High levels were found in the spleen, thymus and brain, while low levels were found in the lungs, heart and liver.

Example 4

Properties of TAK1 kinase

In order to investigate the function of TGF-β-activated kinase in mammalian cells, TAK1 cDNA and TAK1ΔN cDNA were inserted into the mammalian expression vector pEF (H. Shibuya et al., Nature Vol.357, 700 (1992)) under the control of human elongation factor (EF) promoter, to obtain expression plasmids pEF-TAK1 and pEF-TAK1ΔN. The expression plasmids pEF-TAK1 and pEF-TAK1ΔN contain the respective full-length TAK-1-coding and TAK1ΔN-coding sequences, respectively, under the control of EF promoter.

Specifically, the 2.3 kb XhoI fragment of pNV11-HU11 was inserted into the XhoI gap of pBS to obtain pBS-TAK1ΔN. pEF-MSS1 (H. Shibuya et al., Nature Vol.357, 700 (1992)) was cleaved with EcoRI and XbaI, and a synthetic EcoRI-XhoI linker (sense strand: 5'-AATTCGCCACCATGGC-3' (Sequence No.2), antisense strand: 5'-TCGAGCCATGGTGGCG-3' (Sequence No.3) (containing the initiation codon ATG) and XhoI-HindIII and HindIII-XbaI fragments from pBS-TAK1ΔN were inserted therein to prepare pEF-TAK1ΔN. pBS was cleaved with EcoRI and XhoI, and the EcoRI-SacI fragment from pBS-TAK1-5' and the SacI-XhoI fragment from pBS-TAK1ΔN were inserted therein to obtain pBS-TAK1 containing the full-length cDNA of TAK1 (TAK1 cDNA). pEF-MSS1 was cleaved with EcoRI and SalI, and the EcoRI-SacI fragment from pBS-TAK1 was inserted therein to prepare pEF-TAK1.

*E. coli* containing the plasmid pEF-TAK1 and *E. coli* containing the plasmid PEF-TAK1ΔN were internationally deposited as *Escherichia coli* MC1061/P3 (pEF-TAK1) and *Escherichia coli* MC1061/P3 (pEF-TAK1ΔN) at the National Institute of Bioscience and Human Technology Agency of Industrial Scinence and Technology (1-3, 1-chome, Tsukuba City, Ibaraki, Japan) on Sep. 28, 1995 under the respective Assigned Nos. FERM-BP-5246 and FERM-BP-5245, in accordance with the Budapest Treaty.

The TAK1 gene included in plasmid pEF-TAK1 may be cut out using suitable restriction endonucleases such as EcoRI and BamHI.

As a result of testing the effect of TAK1 on induction of gene expression by various ligands, it was discovered that TAK1 has an effect on induction of gene expression by TGF-β. The initial cellular response to TGF-β results in increased levels of mRNA for plasminogen activator inhibitor 1 (PAI-1) (M. R. Keeton et al., J. Biol. Chem. Vol. 266, 23048 (1991)). In order to investigate the effect of TAK1 on the TGF-β response, the TGF-β reporter plasmid p800neoLUC (M. Abe et al., Analyt. Biochem., Vol.216, 276 (1994)) containing the luciferase gene controlled by the PAI-1 promoter induced by TGF-β was used for transient transfection of Mv1Lu lung epithelial cells by the calcium phosphate method (H. Shibuya et al., Nature Vol.357, 700 (1992)). This assay method allows measurement of luciferase activity induced by TGF-β through transfection of Mv1Lu lung epithelial cells with p800neoLUC. The Mv1Lu cells transiently transfected with p800neoLUC responded to TGF-β with 4- to 5-fold reinforced reporter gene activity. The results are shown in the vector column of FIG. 2.

The previously prepared TAK1 and TAK1ΔN expression plasmids were used to transiently transfect Mv1Lu cells together with p800neoLUC. TAK1 expression slightly reinforced TGF-β induced gene expression, and TAK1ΔN constitutively activated PAI-1 gene expression (TAK1ΔN column of FIG. 2). The level of constitutive expression of the reporter gene by TAK1ΔN is comparable to that of the transfectants treated with TGF-β. Hence, activated TAK1 (i.e. TAK1ΔN) can transfer signals in the absence of TGF-β. Furthermore, expression of the PAI-1 gene increased when TGF-β was added to the TAK1ΔN transfectant.

Figure 2:
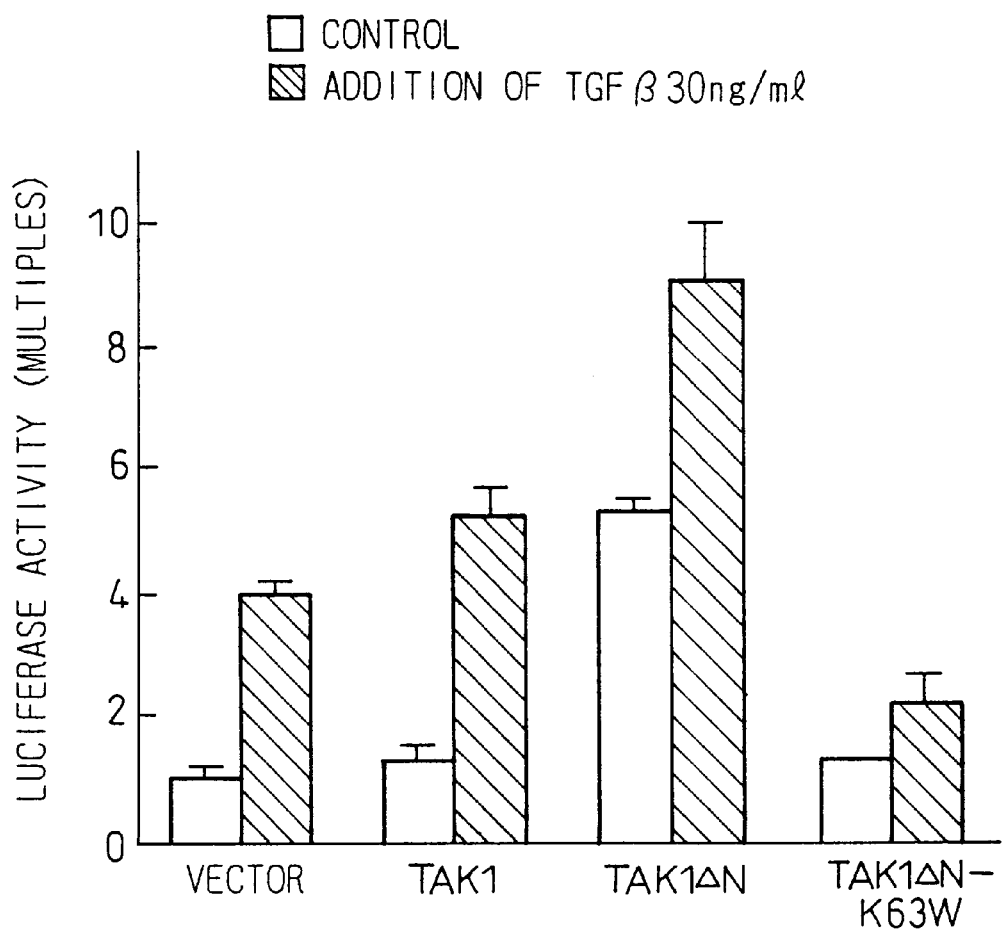
FIG. 2 is a graph showing a result of studying the effect of TGF-β addition on expression of different TAK1 genes, using the luciferase gene as a reporter gene.

In FIG. 2, the white bars represent no induction with TGF-β and the shaded bars represent induction with TGF-β. After transfection in the experiment described above, the cells were cultured for 20 hours in the presence of and in the absence of human TGF-β1 (30 ng/ml), extracts were taken from the cells, and luciferase was measured according to H. Shibuya, et al., Mol. Cell. Biol. Vol.14, 5812 (1994). The graph of FIG. 2 shows relative activities, with 1 being the luciferase activity when cells transformed by the vector (without the TAK1 gene) were not induced by TGF-β1. The results shown in this bar graph represent an average of the results from 3 consecutive experiments.

In order to confirm that these results were mediated by TAK1 kinase activity, catalytically inactive TAK1ΔN-K63W was prepared. This was accomplished using the PCR for site specific mutagenesis. In this vector, the 63rd amino acid lysine of the ATP-binding site is replaced with tryptophan. It is supposed that this mutation destroys TAK1ΔN kinase activity and signal transducing activity. When TAK1ΔN-K63W was simultaneously transfected with p800neoLUC, the ability to constitutively induce PAI-1 gene expression was lost (FIG. 2). This result suggests that TAK1ΔN kinase activity is required for TGF-β-independent expression of the PAI-1 gene. Furthermore, the kinase-negative TAK1ΔN provoked a partial reduction in TGF-β-induced expression. This result supports the belief that TAK1 functions as a mediator in the TGF-β-signal transducing pathway.

In order to obtain direct conclusive proof that TAK1 functions in the TGF-β signal transducing pathway, it was determined whether or not TAK1 kinase activity is activated by treating cells with TGF-β. A suitable foreign substrate was identified by in vitro kinase reaction of TAK1 immunoprecipitated from yeast cells expressing TAK1 labelled with a hemagglutinin (HA) epitope (TAK1-HA) (prepared using the PCR to link the DNA sequence coding for the epitope labelled with anti-HA monoclonal antibody 12CA5 to the 3'-end of DNA coding for TAK1 in the reading frame). Judging from the immunocomplex kinase measurement, the active form of TAK1 was able to phosphorylate and activate the XMEK2/SEK1 subfamily of MAPKK (B. M. Yasher et al., Nature Vol. 372, 794 (1994)). However, no phosphorylation of the original MAPKK-MEK1 (E. Nishida et al., Trends Biochem. Sci., 128 (1993); K. J. Blumer et al., ibid Vol. 19, 286 (1994); R. J. Davis, ibid Vol.19, 470 (1990); C. L. Marchall, Cell, Vol.80, 179 (1995)), histone and myelin basic protein was detected. It is therefore possible to measure TAK1 kinase activity based on its ability to activate XMEK2 in vitro.

The construct for expression of the HA epitope-tagged TAK1 (HA-TAK1) was prepared in the following manner. A synthetic oligonucleotide coding for the HA epitope Tyr-Pro-Tyr-Asp-Val-Pro-Asp-Tyr-Ala (Sequence No.4) labelled with monoclonal antibody 12CA5 was cloned at the SalI site (+3 position from the ATG codon) and EcoRI site of pBS-TAK1 to construct pBS-HA-TAK1. pEF-MSS1 was cleaved with EcoRI and SalI and the EcoRI-XhoI fragment from pBS-HA-TAK1 was inserted therein to construct pEF-HA-TAK1. pBS-HA-TAK1ΔN was constructed by digesting pNV11-HU11 with XhoI and HindIII. The fragment was isolated and inserted at the HincII-HindIII site of pBS-HA-TAK1. pEF-MSS1 was cleaved with EcoRI and SalI and the PstI-XhoI fragment from pBS-HA-TAK1ΔN was inserted therein to construct pEF-HA-TAK1ΔN. Both constructs have two copies of the N-terminal HA epitope expressed from the EF promoter.

The constructs pEF-HA-TAK1 and pEF-HA-TAK1ΔN were used for transient transfection of MC3T3-E1 mouse osteoblasts (S. Ohta et al., FEBS Lett. Vol.314, 356 (1992)). After stimulation with TGF-β, the expressed HA-TAK1 was isolated by immunoprecipitation, and its activity was determined by the coupled kinase assay (S. Matsuda et al., J. Biol. Chem. Vol.270, 12969 (1995)).

Specifically, the transfected cells were treated with TGF-β1 (20 ng/ml) or BMP-4 (100 ng/ml) from 0 (untreated) to 30 minutes. The cells were scraped into a buffer solution (S. Matsuda et al., J. Biol. Chem. Vol.270, 12781 (1995); T. Moriguchi et al., J. Biol. Chem. Vol.270, 12969 (1995)), and the cell extract solution was centrifuged at 15,000×g for 10 minutes. The resulting supernatant was subjected to immunoprecipitation with anti-HA antibody. That is, a 300 μl aliquot of the supernatant was mixed with 20 μl of antibody and 20 μl of protein A Sepharose, and the immunocomplex was washed twice with pBS and used for kinase assay (S. Matsuda et al., J. Biol. Chem. Vol.270, 12781 (1995); T. Moriguchi et al., J. Biol. Chem. Vol.270, 12969 (1995)). The activity is shown as the multiple of increase with respect to the activity of HA-TAK1 from non-stimulated cells. The activity of the immunoprecipitated TAK1 was measured based on ability to activate recombinant XMEX2/SEK1. The activity of XMEX2/SEK1 was measured based on phosphorylation of the recombinant kinase-negative (KN) p38/MPK2 (S. Matsuda et al., J. Biol. Chem. Vol.270, 12781 (1995); T. Moriguchi et al., J. Biol. Chem. Vol.270, 12781 (1995)). It was confirmed that HA-TAK1 does not directly phosphorylate KN-p38/MPK2. The immunoblotting with each of the immunoprecipitating anti-HA antibodies recovered virtually equal amounts of HA-TAK1 at each stage of the immunoprecipitation.

Figure 3:
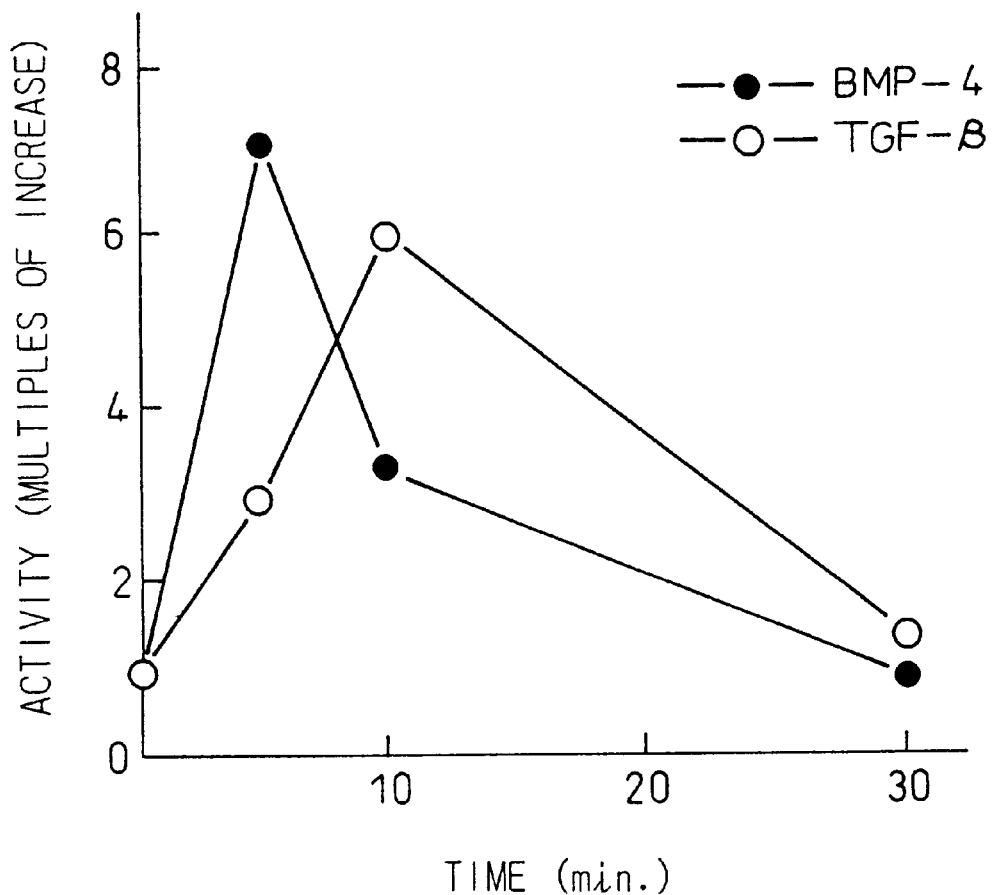
FIG. 3 is a graph showing a result of measuring the effect of TGF-β and BMP-4 on activity of the TAK1 gene in MC3T3 cells, by an immunoprecipitation method and a coupled kinase method.
Figure 4:
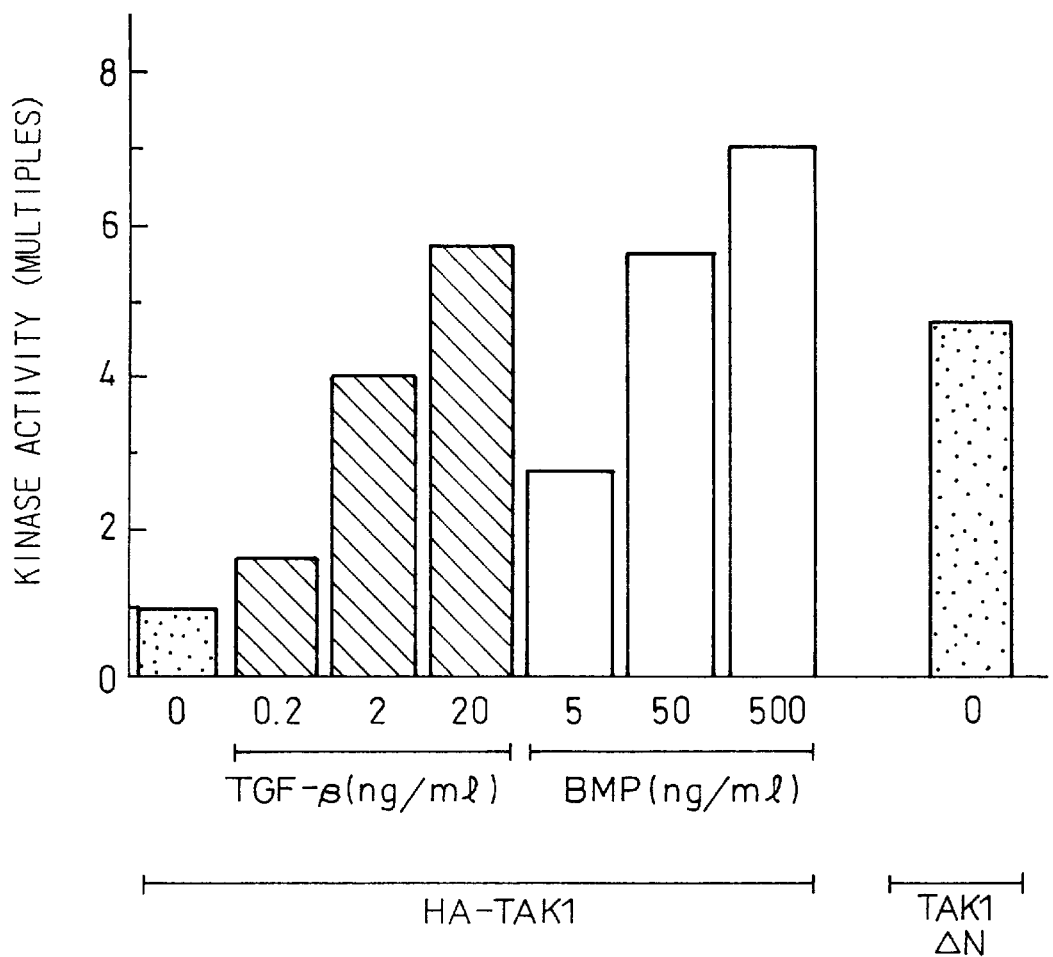
FIG. 4 is a graph showing the effect of various concentrations of TGF-β and BMP-4 on TAK1 kinase activity in cells transfected with the HA-TAK1 gene. The bar denoted as TAK1ΔN represents a result for cells transfected with the TAK1ΔN gene but not stimulated with TGF-β or BMP-4.

The results of the above experiment show that TAK kinase activity began to increase within 5 minutes after stimulation by TGF-β, reached a peak at 10 minutes and returned almost to the baseline within 30 minutes (FIG. 3). In addition, TGF-β1 stimulated TAK1 kinase activity in a dose-dependent manner (FIG. 4). It was next determined whether TAK1 is activated by BMP, a member of the TGF-β superfamily (A. H. Reddi et al., Curr. Opin. Genet. Dev. Vol.4, 737 (1994) or epithelial growth factor (EGF). Interestingly, BMP-4 also activated TAKi kinase in a time- and dose-dependent manner (FIG. 4). On the other hand, no TAK1 activation was observed in cells treated with EGF. It is believed that the reason EGF does not induce TAK1 activation is not that MC3T3-ET cells do not respond to EGF, but rather that the EGF signal does not include TAK1. This is also evident from the fact that EGF induces expression of fos in MC3T3-E1 cells. These data collectively indicate that TAK1 is activated by the TGF-β superfamily.

That TAK1ΔN can activate expression of the PAI-1 gene independently of TGF-β (FIG. 2) suggests that TAK1ΔN protein has increased kinase activity even without TGF-β treatment of cells. To test this possibility, TAK1ΔN labelled with the HA epitope (HA-TAK1ΔN) (see above) was used to transiently transfect MC3T3-E1 cells, and the TAK1N activity was measured by immunocomplex kinase assay. Specifically, the MC3T3-E1 cells were transfected with pEF-HA-TAK1ΔN, the HA-TAK1ΔN was immunoprecipitated from the transfected cells in the manner described earlier, and the activity was measured. All of the data are shown as multiples of increase with respect to activity of HA-TAK1 from non-stimulated cells.

As shown in FIG. 4, the TAK1ΔN protein exhibited higher base kinase activity, supporting the hypothesis that TAK1ΔN which lacks 22 N-terminal amino acid residues is constitutively active.

Example 5

Construction of cDNA library

Poly (A) RNA was prepared from a human cell line Jurkat, and cDNA was synthesized from the poly (A) RNA according to a conventional procedure. The cDNA was inserted into a position downstream of TDH3 promoter in a yeast expression vector pNV7 (J. Ninomiya-Tsuji et al., Proc. Natl. Acad. Sci. USA 88, 9006–9010 (1991)).

Example 6

Screening of cDNA library

A *Saccharomyces cerevisiae* mutant lacking Ssk2/Ssk22 and Shol activities which work in a high osmotic pressure stress signal transducing system can grow in YEPD medium (yeast extract 10 g/l, tryptone 20 g/l, glucose 20 g/l), but cannot grow in the same medium supplemented with 1M sorbitol (T. Maeda et al., Science 269, 554, 1995). Therefore, said yeast mutant can be used to screen the cDNA library. Namely, when said yeast is transformed with cDNA, and if the cDNA comprises a desired gene, the cDNA complements the lacked Ssk1/Ssk2 activities resulting in the growth of the yeast mutant in the sorbitol-containing medium.

For confirmation, *Saccharomyces cerevisiae* (ssk2Δ, ssk22Δ, sho1Δ) lacking Ssk2/Ssk22 and Sho1 activities was transformed with pNV11-HU11 (mouse TAK1ΔN) obtained in Example 2, and the transformed yeast cells were plated on a YEPD medium plate containing 1M sorbitol and incubated at 30° C. As a result, the yeast cells transformed with pNV11-HU11 grew under high osmotic pressure stress. This experiment confirmed that the screening system is effective.

Accordingly, *Saccharomyces cerevisiae* (ssk2Δ, ssk22Δ, sho1Δ) was transformed with the cDNA library constructed in Example 5, and the transformant was screened under a high osmotic pressure stress by incubating the transformant in a YEPD medium containing 1M sorbitol at 30° C., so as to obtain one positive clone, pNV7-hTAK1. A cDNA contained in this clone was amplified by PRISM Dye Terminator Cycle Sequencing kit (Perkin Elmer) and sequenced. The nucleotide sequence thus determined and a corresponding amino acid sequence is shown in SEQ ID NO: 5. This nucleotide sequence of cDNA derived from human shows 92% homology with nucleotide sequence of mouse TAK1, and the human amino acid sequence shows 99% homology with the amino acid sequence of mouse TAK1. FIGS. 5A to 5E and FIGS. 6A to 6B compose nucleotide sequence and amino acid sequence, respectively, of mouse TAK1 and those of human TAK1. The human TAK1 cDNA was subcloned into pUC19 digested with SalI to obtain phTAK1 containing the full-length of cDNA of the human TAK1. *E. coli* containing the plasmid phTAKl was internationally deposited as *Escherichia coli* JM109 (phTAK1) at the National Institute of Bioscience and Human Technology Agency of Industrial Science and Technology (1-3, 1-chome, Tsukuba City, Ibaraki, Japan) on Jul. 19, 1996 under the Assigned No. FERM-BP-5598 in accordance with the Budapest Treaty.

Depositing of microorganisms

The following microorganisms were deposited at the Patent Microorganisms Depository Center of the National Institute of the Bioscience and Human Technology Agency of Industrial Science and Technology (1-3, 1-chome, Tsukuba City, Ibaraki, Japan) on Sep. 28, 1995, under the Assigned Nos. listed below.

Name: *Escherichia coli* MC1061/P3 (pEF-TAK1) Date of deposit: Sep. 28, 1995 Assigned No.: FERM-BP-5246

Name: *Escherichia coli* MC1061/P3 (pEF-TAK1ΔN) Date of deposit: Sep. 28, 1995 Assigned No.: FERM-BP-5245

Name: *Escherichia coli* JM109 (phTAK1) Date of deposite: Jul. 19, 1996 Assigned No.: FERM BP-5598

---

We claim:

1. An isolated DNA coding for a polypeptide with kinase activity which is activated by transforming growth factor (TGF)-β and comprises the amino acid sequence of SEQ ID NO: 1 from Ser at position 23 to Ser at position 579.

2. An isolated DNA according to claim 1 which has the nucleotide sequence of SEQ ID NO: 1 from T at position 223 to A at position 1893.

3. A method of producing a polypeptide with kinase activity which is activated by TGF-β, characterized by culturing host cells transformed with a vector comprising DNA according to claim 1, and collecting the expressed product from the culture.

4. A polypeptide with kinase activity which is activated by TGF-β, and which is produced according to the method of claim 3.

5. A vector comprising a DNA according to claim 1.

6. A host transformed with a vector according to claim 5.

7. An isolated DNA coding for a polypeptide with kinase activity which is activated by TGF-β and comprises the amino acid sequence of SEQ ID NO: 1 from Met at position 1 to Ser at position 579.

8. An isolated DNA according to claim 2 which has the nucleotide sequence of SEQ ID NO: 1 from A at position 157 to A at position 1893.

9. A method of producing a polypeptide with kinase activity which is activated by TGF-β, characterized by culturing host cells transformed with a vector comprising DNA according to claim 7, and collecting the expressed product from the culture.

10. A vector comprising a DNA according to claim 7.

11. A host transformed with a vector according to claim 10.

12. An isolated DNA coding for a polypeptide with kinase activity which is activated by TGF-β and is capable of hybridizing with the nucleotide sequence complementary to SEQ ID NO: 1 under conditions of 60° C., 0.1×SSC and 0.1% SDS.

13. An isolated DNA according to claim 6 which has the nucleotide sequence of SEQ ID NO: 5.

14. A method of producing a polypeptide with kinase activity which is activated by TGF-β, characterized by culturing host cells transformed with a vector comprising DNA according to claim 12, and collecting the expressed product from the culture.

15. An isolated DNA coding for a polypeptide with kinase activity which is activated by TGF-β and comprises the amino acid sequence of SEQ ID NO: 5 from Ser at position 23 to Ser at position 579.

16. An isolated DNA according to claim 14 which has the nucleotide sequence of SEQ ID NO: 5 from T at position 249 to A at position 1919.

17. A method of producing a polypeptide with kinase activity which is activated by TGF-β, characterized by culturing host cells transformed with a vector comprising DNA according to claim 15, and collecting the expressed product from the culture.

18. A vector comprising a DNA according to claim 15.

19. A host transformed with a vector according to claim 18.

20. An isolated DNA coding for a polypeptide with kinase activity which is activated by TGF-β and comprises the amino acid sequence of SEQ ID NO:5 from Met at position 1 to Ser at position 579.

21. An isolated DNA according to claim 20 which has the nucleotide sequence of SEQ ID NO: 5 from A at position 183 to A at position 1919.

22. A method of producing a polypeptide with kinase activity which is activated by TGF-β, characterized by culturing host cells transformed with a vector comprising DNA according to claim 20, and collecting the expressed product from the culture.

23. A vector comprising a DNA according to claim 20.

24. A host transformed with a vector according to claim 23.

25. An isolated DNA coding for a polypeptide with kinase activity which is activated by TGF-β and is capable of hybridizing with the nucleotide sequence complementary to SEQ ID NO: 5 under conditions of 60° C., 0.1×SSC and 0.1% SDS.

26. A method of producing a polypeptide with kinase activity which is activated by TGF-β, characterized by culturing host cells transformed with a vector comprising DNA according to claim 25, and collecting the expressed product from the culture.

27. An isolated kinase which is activated by TGF-β and has the amino acid sequence of SEQ ID NO: 1 from Ser at position 23 to Ser at position 579.

28. An isolated kinase which is activated by TGF-β and has the amino acid sequence of SEQ ID NO: 5 from Ser at position 23 to Ser at position 579.

29. An isolated DNA coding for a fusion protein which comprises:

a first polypeptide having kinase activity which is activated by transforming growth factor (TGF)-β and comprises the amino acid sequence of SEQ ID NO: 1 from Ser at position 23 to Ser at position 579; and a second polypeptide.

30. A vector comprising a DNA according to claim 29.

31. A host transformed with a vector according to claim 30.

32. An isolated DNA coding for a fusion protein which comprises:

a first polypeptide having kinase activity which is activated by TGF-β and comprises the amino acid sequence of SEQ ID NO:1 from Met at position 1 to Ser at position 579; and a second polypeptide.

33. A vector comprising a DNA according to claim 32.

34. A host transformed with a vector according to claim 33.

35. An isolated DNA coding for a fusion protein comprising:

a first polypeptide having kinase activity which is activated by TGF-β and comprises the amino acid sequence of SEQ ID NO: 5 from Ser at position 23 to Ser at position 579; and a second polypeptide.

36. A vector comprising a DNA according to claim 35.

37. A host transformed with a vector according to claim 36.

38. An isolated DNA coding for a fusion protein comprising:

a first polypeptide with kinase activity which is activated by TGF-β and comprises the amino acid sequence of SEQ ID NO:5 from Met at position 1 to Ser at position 579; and a second polypeptide.

39. A vector comprising a DNA according to claim 38.

40. A host transformed with a vector according to claim 39.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 2443 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: CDS
      (B) LOCATION: 157..1893

(xi) SEQUENCE DESCRIPTION: SEQ ID NO:1:

```
GAATTCGGCA CGAGGAGGAG CCGAAGCCGG GACTCGGCGG TGGCCCGGGT CGGTCCCGCG        60

CCACGGAGCG CCGGGCGGCG GGCTGCGGGG CTCCGGGCTG AAGGGCGCTG CGCGAGCCGG       120

AGGGCGGGCG CGGCCCCCCG GGCGCCGCGG GGGATC ATG TCG ACA GCC TCC GCC        174
                                       Met Ser Thr Ala Ser Ala
                                         1               5

GCC TCG TCC TCC TCC TCG TCT TCT GCC AGT GAG ATG ATC GAA GCG CCG        222
Ala Ser Ser Ser Ser Ser Ser Ser Ala Ser Glu Met Ile Glu Ala Pro
             10                  15                  20

TCG CAG GTC CTG AAC TTC GAA GAG ATC GAC TAC AAG GAG ATC GAG GTG        270
Ser Gln Val Leu Asn Phe Glu Glu Ile Asp Tyr Lys Glu Ile Glu Val
         25                  30                  35

GAA GAG GTT GTC GGA AGA GGA GCT TTT GGA GTA GTT TGC AAA GCT AAG        318
Glu Glu Val Val Gly Arg Gly Ala Phe Gly Val Val Cys Lys Ala Lys
     40                  45                  50
```

-continued

| | | |
|---|---|---|
| TGG AGA GCA AAA GAT GTC GCT ATT AAA CAG ATA GAA AGT GAG TCT GAG<br>Trp Arg Ala Lys Asp Val Ala Ile Lys Gln Ile Glu Ser Glu Ser Glu<br>55                       60                   65                 70 | 366 |

```
TGG AGA GCA AAA GAT GTC GCT ATT AAA CAG ATA GAA AGT GAG TCT GAG        366
Trp Arg Ala Lys Asp Val Ala Ile Lys Gln Ile Glu Ser Glu Ser Glu
 55                  60                  65                  70

AGG AAG GCT TTC ATT GTG GAG CTC CGG CAG TTG TCG CGT GTG AAC CAT        414
Arg Lys Ala Phe Ile Val Glu Leu Arg Gln Leu Ser Arg Val Asn His
             75                  80                  85

CCT AAC ATT GTC AAG TTG TAC GGA GCC TGC CTG AAT CCA GTA TGT CTT        462
Pro Asn Ile Val Lys Leu Tyr Gly Ala Cys Leu Asn Pro Val Cys Leu
                 90                  95                 100

GTG ATG GAA TAT GCA GAG GGG GGC TCA TTG TAT AAT GTG CTG CAT GGT        510
Val Met Glu Tyr Ala Glu Gly Gly Ser Leu Tyr Asn Val Leu His Gly
            105                 110                 115

GCT GAA CCA TTG CCT TAC TAC ACT GCT GCT CAT GCC ATG AGC TGG TGT        558
Ala Glu Pro Leu Pro Tyr Tyr Thr Ala Ala His Ala Met Ser Trp Cys
    120                 125                 130

TTA CAG TGT TCC CAA GGA GTG GCT TAC CTG CAC AGC ATG CAG CCC AAA        606
Leu Gln Cys Ser Gln Gly Val Ala Tyr Leu His Ser Met Gln Pro Lys
135                 140                 145                 150

GCG CTG ATT CAC AGG GAC CTC AAG CCT CCA AAC TTG CTG CTG GTT GCA        654
Ala Leu Ile His Arg Asp Leu Lys Pro Pro Asn Leu Leu Leu Val Ala
                155                 160                 165

GGA GGG ACA GTT CTA AAA ATC TGC GAT TTT GGT ACA GCT TGT GAC ATC        702
Gly Gly Thr Val Leu Lys Ile Cys Asp Phe Gly Thr Ala Cys Asp Ile
            170                 175                 180

CAA ACA CAC ATG ACC AAT AAT AAA GGG AGT GCT GCT TGG ATG GCG CCT        750
Gln Thr His Met Thr Asn Asn Lys Gly Ser Ala Ala Trp Met Ala Pro
        185                 190                 195

GAA GTG TTT GAA GGT AGC AAT TAC AGT GAA AAG TGT GAT GTC TTC AGC        798
Glu Val Phe Glu Gly Ser Asn Tyr Ser Glu Lys Cys Asp Val Phe Ser
    200                 205                 210

TGG GGT ATT ATC CTC TGG GAA GTG ATA ACA CGC CGG AAA CCC TTC GAT        846
Trp Gly Ile Ile Leu Trp Glu Val Ile Thr Arg Arg Lys Pro Phe Asp
215                 220                 225                 230

GAG ATC GGT GGC CCA GCT TTC AGA ATC ATG TGG GCT GTT CAT AAT GGC        894
Glu Ile Gly Gly Pro Ala Phe Arg Ile Met Trp Ala Val His Asn Gly
                235                 240                 245

ACT CGA CCA CCA CTG ATC AAA AAT TTA CCT AAG CCC ATT GAG AGC TTG        942
Thr Arg Pro Pro Leu Ile Lys Asn Leu Pro Lys Pro Ile Glu Ser Leu
            250                 255                 260

ATG ACA CGC TGT TGG TCT AAG GAC CCA TCT CAG CGC CCT TCA ATG GAG        990
Met Thr Arg Cys Trp Ser Lys Asp Pro Ser Gln Arg Pro Ser Met Glu
        265                 270                 275

GAA ATT GTG AAA ATA ATG ACT CAC TTG ATG CGG TAC TTC CCA GGA GCG       1038
Glu Ile Val Lys Ile Met Thr His Leu Met Arg Tyr Phe Pro Gly Ala
    280                 285                 290

GAT GAG CCA TTA CAG TAT CCT TGT CAC TAC TCT GAT GAA GGG CAG AGC       1086
Asp Glu Pro Leu Gln Tyr Pro Cys His Tyr Ser Asp Glu Gly Gln Ser
295                 300                 305                 310

AAC TCA GCC ACC AGC ACA GGC TCG TTC ATG GAC ATT GCT TCT ACA AAT       1134
Asn Ser Ala Thr Ser Thr Gly Ser Phe Met Asp Ile Ala Ser Thr Asn
                315                 320                 325

ACC AGT AAT AAA AGT GAC ACA AAT ATG GAA CAG GTT CCT GCC ACA AAC       1182
Thr Ser Asn Lys Ser Asp Thr Asn Met Glu Gln Val Pro Ala Thr Asn
            330                 335                 340

GAC ACT ATT AAA CGC TTG GAG TCA AAA CTG TTA AAA AAC CAG GCA AAG       1230
Asp Thr Ile Lys Arg Leu Glu Ser Lys Leu Leu Lys Asn Gln Ala Lys
        345                 350                 355

CAA CAG AGT GAA TCT GGA CGC CTG AGC TTG GGA GCC TCT CGT GGG AGC       1278
Gln Gln Ser Glu Ser Gly Arg Leu Ser Leu Gly Ala Ser Arg Gly Ser
    360                 365                 370
```

```
AGT GTG GAG AGC TTG CCC CCC ACT TCC GAG GGC AAG AGG ATG AGT GCT      1326
Ser Val Glu Ser Leu Pro Pro Thr Ser Glu Gly Lys Arg Met Ser Ala
375                 380                 385                 390

GAC ATG TCT GAA ATA GAA GCC AGG ATC GTG GCG ACT GCA GGT AAC GGG      1374
Asp Met Ser Glu Ile Glu Ala Arg Ile Val Ala Thr Ala Gly Asn Gly
                395                 400                 405

CAA CCA AGG CGT AGA TCC ATC CAA GAC TTG ACT GTT ACT GGG ACA GAA      1422
Gln Pro Arg Arg Arg Ser Ile Gln Asp Leu Thr Val Thr Gly Thr Glu
            410                 415                 420

CCT GGT CAG GTG AGC AGC CGG TCA TCC AGC CCT AGT GTC AGA ATG ATC      1470
Pro Gly Gln Val Ser Ser Arg Ser Ser Ser Pro Ser Val Arg Met Ile
        425                 430                 435

ACT ACC TCA GGA CCA ACC TCA GAG AAG CCA GCT GCG AGT CAC CCA TGG      1518
Thr Thr Ser Gly Pro Thr Ser Glu Lys Pro Ala Ala Ser His Pro Trp
440                 445                 450

ACC CCT GAT GAT TCC ACA GAC ACC AAT GGC TCA GAT AAC TCC ATC CCA      1566
Thr Pro Asp Asp Ser Thr Asp Thr Asn Gly Ser Asp Asn Ser Ile Pro
455                 460                 465                 470

ATG GCG TAT CTT ACA CTG GAT CAC CAG CTA CAG CCT CTA GCG CCG TGC      1614
Met Ala Tyr Leu Thr Leu Asp His Gln Leu Gln Pro Leu Ala Pro Cys
                475                 480                 485

CCA AAC TCC AAA GAA TCC ATG GCA GTG TTC GAA CAG CAC TGT AAA ATG      1662
Pro Asn Ser Lys Glu Ser Met Ala Val Phe Glu Gln His Cys Lys Met
            490                 495                 500

GCA CAG GAG TAT ATG AAA GTT CAA ACC GAA ATC GCA TTG TTA CTA CAG      1710
Ala Gln Glu Tyr Met Lys Val Gln Thr Glu Ile Ala Leu Leu Leu Gln
        505                 510                 515

AGA AAG CAA GAA CTA GTT GCA GAA TTG GAC CAG GAT GAA AAG GAC CAG      1758
Arg Lys Gln Glu Leu Val Ala Glu Leu Asp Gln Asp Glu Lys Asp Gln
520                 525                 530

CAA AAT ACA TCT CGT CTG GTA CAG GAA CAT AAA AAG CTT TTA GAT GAA      1806
Gln Asn Thr Ser Arg Leu Val Gln Glu His Lys Lys Leu Leu Asp Glu
535                 540                 545                 550

AAC AAA AGC CTT TCT ACT TAT TAC CAG CAA TGC AAA AAA CAA CTA GAG      1854
Asn Lys Ser Leu Ser Thr Tyr Tyr Gln Gln Cys Lys Lys Gln Leu Glu
                555                 560                 565

GTC ATC AGA AGC CAA CAG CAG AAA CGA CAA GGC ACT TCA TGATTCTCTG       1903
Val Ile Arg Ser Gln Gln Gln Lys Arg Gln Gly Thr Ser
            570                 575

GGACCGTTAC GTTTTAAAAT ATGCAAAGAC CTTTTTTTAA GAGAAGACAA ACCATTATAA    1963

CAGTTCATGA GTGTTAGCTT TTTGGCGTGT TCTGAATGCC AAATGCCTCT CTTTGCTGCA    2023

TTTGTTATGT CAGTTACCTT TCTTCTTATG GTGGATATAA AATCCACTGT CGTGTTGCAG    2083

CAGATGATGG CACCTGTGGC TTGGGAAGGC GAGCGTGCTC AGCTTCAGGG GCACATGAAG    2143

TGAACCTGGC TGTATGTGCA TGCTCCTGGA GTGAGCTACC TAACAGGAGG GGGTAGCACA    2203

CTGGCTACTG TGTGCAGGCA TCATCCTTTC TCTGTAGTAA AAGGTGGGAC CTCAAGAATT    2263

TTCTTCAAAG TGCTCATCTC AAAAATCTGA TTTTTTTCCC AGTAGATGGT ATGCTCCAAT    2323

GTAAAGACAG AGTATTAAAA TAACTTGTGG TACATTACAG AGGGACAGAA TGTTGAGGCT    2383

GAGTTCAAAG ACAGGGTTTG TGCCAACACA TCCTGGCTTT AGAGCACAAT GGATCTCGAG    2443
```

(2) INFORMATION FOR SEQ ID NO:2:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:2:

AATTCGCCAC CATGGC                                                                       16

(2) INFORMATION FOR SEQ ID NO:3:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

TCGAGCCATG GTGGCG                                                                       16

(2) INFORMATION FOR SEQ ID NO:4:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Tyr Pro Tyr Asp Val Pro Asp Tyr Ala
1               5

(2) INFORMATION FOR SEQ ID NO:5:

(i) SEQUENCE CHARACTERISTICS:
        (A) LENGTH: 2656 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 183..1922

(xi) SEQUENCE DESCRIPTION: SEQ ID NO:5:

```
GTCGAGATCC ATTGTGCTCT AAAGACGGCT GTGGCCGCTG CCTCTACCCC CGCCACGGAT          60

CGCCGGGTAG TAGGACTGCG CGGCTCCAGG CTGAGGGTCG GTCCGGAGGC GGGTGGGCGC         120

GGGTCTCACC CGGATTGTCC GGGTGGCACC GTTCCCGGCC CCACCGGGCG CCGCGAGGGA         180

TC ATG TCT ACA GCC TCT GCC GCC TCC TCC TCC TCC TCG TCT TCG GCC            227
   Met Ser Thr Ala Ser Ala Ala Ser Ser Ser Ser Ser Ser Ala
     1               5                  10                  15

GGT GAG ATG ATC GAA GCC CCT TCC CAG GTC CTC AAC TTT GAA GAG ATC           275
Gly Glu Met Ile Glu Ala Pro Ser Gln Val Leu Asn Phe Glu Glu Ile
                20                  25                  30

GAC TAC AAG GAG ATC GAG GTG GAA GAG GTT GTT GGA AGA GGA GCC TTT           323
Asp Tyr Lys Glu Ile Glu Val Glu Glu Val Val Gly Arg Gly Ala Phe
                    35                  40                  45

GGA GTT GTT TGC AAA GCT AAG TGG AGA GCA AAA GAT GTT GCT ATT AAA           371
Gly Val Val Cys Lys Ala Lys Trp Arg Ala Lys Asp Val Ala Ile Lys
                50                  55                  60

CAA ATA GAA AGT GAA TCT GAG AGG AAA GCG TTT ATT GTA GAG CTT CGG           419
Gln Ile Glu Ser Glu Ser Glu Arg Lys Ala Phe Ile Val Glu Leu Arg
            65                  70                  75

CAG TTA TCC CGT GTG AAC CAT CCT AAT ATT GTA AAG CTT TAT GGA GCC           467
```

```
        Gln Leu Ser Arg Val Asn His Pro Asn Ile Val Lys Leu Tyr Gly Ala
         80                  85                  90                  95

TGC TTG AAT CCA GTG TGT CTT GTG ATG GAA TAT GCT GAA GGG GGC TCT          515
Cys Leu Asn Pro Val Cys Leu Val Met Glu Tyr Ala Glu Gly Gly Ser
                100                 105                 110

TTA TAT AAT GTG CTG CAT GGT GCT GAA CCA TTG CCA TAT TAT ACT GCT          563
Leu Tyr Asn Val Leu His Gly Ala Glu Pro Leu Pro Tyr Tyr Thr Ala
                115                 120                 125

GCC CAC GCA ATG AGT TGG TGT TTA CAG TGT TCC CAA GGA GTG GCT TAT          611
Ala His Ala Met Ser Trp Cys Leu Gln Cys Ser Gln Gly Val Ala Tyr
            130                 135                 140

CTT CAC AGC ATG CAA CCC AAA GCG CTA ATT CAC AGG GAC CTG AAA CCA          659
Leu His Ser Met Gln Pro Lys Ala Leu Ile His Arg Asp Leu Lys Pro
        145                 150                 155

CCA AAC TTA CTG CTG GTT GCA GGG GGG ACA GTT CTA AAA ATT TGT GAT          707
Pro Asn Leu Leu Leu Val Ala Gly Gly Thr Val Leu Lys Ile Cys Asp
160                 165                 170                 175

TTT GGT ACA GCC TGT GAC ATT CAG ACA CAC ATG ACC AAT AAC AAG GGG          755
Phe Gly Thr Ala Cys Asp Ile Gln Thr His Met Thr Asn Asn Lys Gly
                180                 185                 190

AGT GCT GCT TGG ATG GCA CCT GAA GTT TTT GAA GGT AGT AAT TAC AGT          803
Ser Ala Ala Trp Met Ala Pro Glu Val Phe Glu Gly Ser Asn Tyr Ser
            195                 200                 205

GAA AAA TGT GAC GTC TTC AGC TGG GGT ATT ATT CTT TGG GAA GTG ATA          851
Glu Lys Cys Asp Val Phe Ser Trp Gly Ile Ile Leu Trp Glu Val Ile
        210                 215                 220

ACG CGT CGG AAA CCC TTT GAT GAG ATT GGT GGC CCA GCT TTC CGA ATC          899
Thr Arg Arg Lys Pro Phe Asp Glu Ile Gly Gly Pro Ala Phe Arg Ile
    225                 230                 235

ATG TGG GCT GTT CAT AAT GGT ACT CGA CCA CCA CTG ATA AAA AAT TTA          947
Met Trp Ala Val His Asn Gly Thr Arg Pro Pro Leu Ile Lys Asn Leu
240                 245                 250                 255

CCT AAG CCC ATT GAG AGC CTG ATG ACT CGT TGT TGG TCT AAA GAT CCT          995
Pro Lys Pro Ile Glu Ser Leu Met Thr Arg Cys Trp Ser Lys Asp Pro
                260                 265                 270

TCC CAG CGC CCT TCA ATG GAG GAA ATT GTG AAA ATA ATG ACT CAC TTG         1043
Ser Gln Arg Pro Ser Met Glu Glu Ile Val Lys Ile Met Thr His Leu
            275                 280                 285

ATG CGG TAC TTT CCA GGA GCA GAT GAG CCA TTA CAG TAT CCT TGT CAG         1091
Met Arg Tyr Phe Pro Gly Ala Asp Glu Pro Leu Gln Tyr Pro Cys Gln
        290                 295                 300

TAT TCA GAT GAA GGA CAG AGC AAC TCT GCC ACC AGT ACA GGC TCA TTC         1139
Tyr Ser Asp Glu Gly Gln Ser Asn Ser Ala Thr Ser Thr Gly Ser Phe
    305                 310                 315

ATG GAC ATT GCT TCT ACA AAT ACG AGT AAC AAA AGT GAC ACT AAT ATG         1187
Met Asp Ile Ala Ser Thr Asn Thr Ser Asn Lys Ser Asp Thr Asn Met
320                 325                 330                 335

GAG CAA GTT CCT GCC ACA AAT GAT ACT ATT AAG CGC TTA GAA TCA AAA         1235
Glu Gln Val Pro Ala Thr Asn Asp Thr Ile Lys Arg Leu Glu Ser Lys
                340                 345                 350

TTG TTG AAA AAT CAG GCA AAG CAA CAG AGT GAA TCT GGA CGT TTA AGC         1283
Leu Leu Lys Asn Gln Ala Lys Gln Gln Ser Glu Ser Gly Arg Leu Ser
            355                 360                 365

TTG GGA GCC TCC CAT GGG AGC AGT GTG GAG AGC TTG CCC CCA ACC TCT         1331
Leu Gly Ala Ser His Gly Ser Ser Val Glu Ser Leu Pro Pro Thr Ser
        370                 375                 380

GAG GGC AAG AGG ATG AGT GCT GAC ATG TCT GAA ATA GAA GCT AGG ATC         1379
Glu Gly Lys Arg Met Ser Ala Asp Met Ser Glu Ile Glu Ala Arg Ile
    385                 390                 395

GCC GCA ACC ACA GGC AAC GGA CAG CCA AGA CGT AGA TCC ATC CAA GAC         1427
```

```
               Ala Ala Thr Thr Gly Asn Gly Gln Pro Arg Arg Arg Ser Ile Gln Asp
               400             405             410             415

TTG ACT GTA ACT GGA ACA GAA CCT GGT CAG GTG AGC AGT AGG TCA TCC               1475
Leu Thr Val Thr Gly Thr Glu Pro Gly Gln Val Ser Ser Arg Ser Ser
                420             425             430

AGT CCC AGT GTC AGA ATG ATT ACT ACC TCA GGA CCA ACC TCA GAA AAG               1523
Ser Pro Ser Val Arg Met Ile Thr Thr Ser Gly Pro Thr Ser Glu Lys
            435             440             445

CCA ACT CGA AGT CAT CCA TGG ACC CCT GAT GAT TCC ACA GAT ACC AAT               1571
Pro Thr Arg Ser His Pro Trp Thr Pro Asp Asp Ser Thr Asp Thr Asn
            450             455             460

GGA TCA GAT AAC TCC ATC CCA ATG GCT TAT CTT ACA CTG GAT CAC CAA               1619
Gly Ser Asp Asn Ser Ile Pro Met Ala Tyr Leu Thr Leu Asp His Gln
            465             470             475

CTA CAG CCT CTA GCA CCG TGC CCA AAC TCC AAA GAA TCT ATG GCA GTG               1667
Leu Gln Pro Leu Ala Pro Cys Pro Asn Ser Lys Glu Ser Met Ala Val
480             485             490             495

TTT GAA CAG CAT TGT AAA ATG GCA CAA GAA TAT ATG AAA GTT CAA ACA               1715
Phe Glu Gln His Cys Lys Met Ala Gln Glu Tyr Met Lys Val Gln Thr
                500             505             510

GAA ATT GCA TTG TTA TTA CAG AGA AAG CAA GAA CTA GTT GCA GAA CTG               1763
Glu Ile Ala Leu Leu Leu Gln Arg Lys Gln Glu Leu Val Ala Glu Leu
                515             520             525

GAC CAG GAT GAA AAG GAC CAG CAA AAT ACA TCT CGC CTG GTA CAG GAA               1811
Asp Gln Asp Glu Lys Asp Gln Gln Asn Thr Ser Arg Leu Val Gln Glu
            530             535             540

CAT AAA AAG CTT TTA GAT GAA AAC AAA AGC CTT TCT ACT TAC TAC CAG               1859
His Lys Lys Leu Leu Asp Glu Asn Lys Ser Leu Ser Thr Tyr Tyr Gln
            545             550             555

CAA TGC AAA AAA CAA CTA GAG GTC ATC AGA AGT CAG CAG CAG AAA CGA               1907
Gln Cys Lys Lys Gln Leu Glu Val Ile Arg Ser Gln Gln Gln Lys Arg
560             565             570             575

CAA GGC ACT TCA TGA TTCTCTGGGA CCGTTACATT TTGAAATATG CAAAGAAAGA              1962
Gln Gly Thr Ser  *
                580

CTTTTTTTTT AAGGAAAGGA AAACCTTATA ATGACGATTC ATGAGTGTTA GCTTTTTGGC             2022

GTGTTCTGAA TGCCAACTGC CTATATTTGC TGCATTTTTT TCATTGTTTA TTTTCCTTTT             2082

CTCATGGTGG ACATACAATT TTACTGTTTC ATTGCATAAC ATGGTAGCAT CTGTGACTTG             2142

AATGAGCAGC ACTTTGCAAC TTCAAAACAG ATGCAGTGAA CTGTGGCTGT ATATGCATGC             2202

TCATTGTGTG AAGGCTAGCC TAACAGAACA GGAGGTATCA AACTAGCTGC TATGTGCAAA             2262

CAGCGTCCAT TTTTTCATAT TAGAGGTGGA ACCTCAAGAA TGACTTTATT CTTGTATCTC             2322

ATCTCAAAAT ATTAATAATT TTTTTCCCAA AAGATGGTAT ATACCAAGTT AAAGACAGGG             2382

TATTATAAAT TTAGAGTGAT TGGTGGTATA TTACGGAAAT ACGGAACCTT TAGGGATAGT             2442

TCCGTGTAAG GGCTTTGATG CCAGCATCCT TGGATCAGTA CTGAACTCAG TTCCATCCGT             2502

AAAATATGTA AAGGTAAGTG GCAGCTGCTC TATTTAATGA AAGCAGTTTT ACCGGATTTT             2562

GTTAGACTAA AATTTGATTG TGATACATTG AACAAAATGG AACTCATTTT TTTTAAGGAG             2622

TAAAGATTTT CTTTAGAGCA CAATGGATCT CGAC                                        2656
```